US00PP17765P3

(12) United States Plant Patent
Hanes

(10) Patent No.: US PP17,765 P3
(45) Date of Patent: May 29, 2007

(54) ***VERBENA* PLANT NAMED 'RAP HOROSE'**

(50) Latin Name: ***Verbena hybrida*×*Verbena tenuisecta***
Varietal Denomination: Rap Horose

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 323 days.

(21) Appl. No.: 11/094,747

(22) Filed: Mar. 31, 2005

(65) Prior Publication Data

US 2006/0225174 P1 Oct. 5, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—June Hwu
(74) *Attorney, Agent, or Firm*—Jondle & Associates P.C

(57) ABSTRACT

A *verbena* cultivar particularly distinguished by its rose-colored flowers, upright habit and mildew tolerance is disclosed.

1 Drawing Sheet

Figure 1:
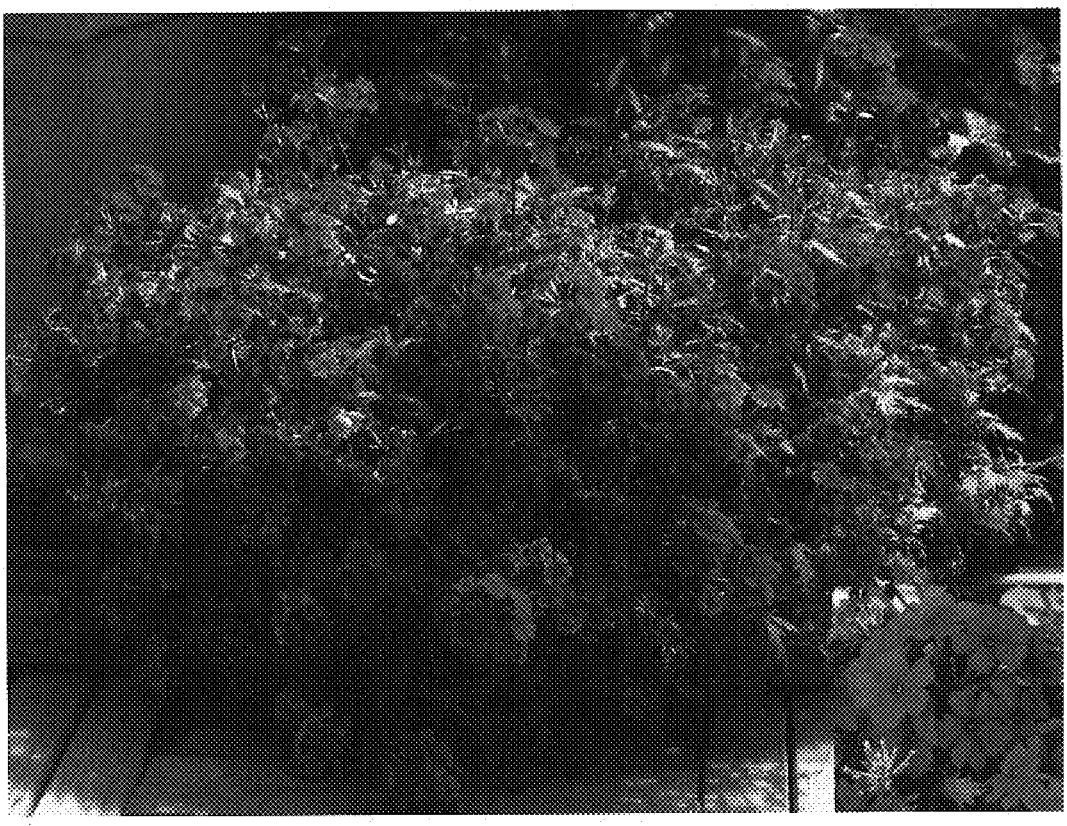

Genus and species: *Verbena hybrida*×*Verbena tenuisecta.* Variety denomination: 'Rap Horose'.

BACKGROUND OF THE NEW PLANT

The present invention comprises a new and distinct cultivar of *verbena,* botanically known as *Verbena hybrida*× *Verbena tenuisecta,* and hereinafter referred to by the cultivar name 'Rap Horose'. The new cultivar originated from a hybridzation made in the year 2002 in Gilroy, Calif. The female parent was 'Oxena' (also known as 'Babylon Red') (U.S. Plant Pat. No. 13,126) while the male parent was '1352-1', a purple proprietary *verbena* line (unpatented).

The new cultivar was created in 2002 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif., Litchfield, Mich. and Andijk, The Netherlands. The present invention has been found to retain its distinctive characteristics through successive asexual propagations.

DESCRIPTION OF PHOTOGRAPH

This new *verbena* plant is illustrated by the accompanying photograph which shows overall plant habit, flowers, and foliage of the plant; the colors shown are as true as can be reasonably obtained by conventional photographic procedures.

FIG. 1. The photograph shows overall plant habit, flowers, and foliage; the inset shows mature inflorescences.

DESCRIPTION OF THE NEW CULTIVAR

The following detailed descriptions set forth the distinctive characteristics of 'Rap Horose'. The data which define these characteristics were collected from asexual reproductions carried out in Gilroy, Calif. The plant history was taken on 5-month-old plants grown in one-gallon pots in a poly-covered greenhouse in the fall/winter season. Color readings were taken in the greenhouse in the late winter season under natural light. Color references are primarily to The R.H.S. Colour Chart of The Royal Horticultural Society of London (R.H.S.) (2001 edition). Texture description details were observed with a dissecting microscope.

DETAILED BOTANICAL DESCRIPTION

Classification:
- *Botanical.*—*Verbena hybrida*×*Verbena tenuisecta.*
- *Common name.*—*Verbena.*

Growth:
- *Form.*—Low trailing annual, decumbent.
- *Growth and branching habit.*—Vigorous growing, moderate basal branching, trailing habit.
- *Height.*—5.0–7.0 cm as measured from the top of the soil excluding flowers.
- *Width.*—35.0–50.0 cm excluding flowers.
- *Time to produce a finished flowering plant.*—8–10 weeks.
- *Outdoor plant performance.*—Typical bedding plant culture; full-sun in the garden, hanging baskets, or container plants.
- *Time to initiate and develop roots.*—4–10 days.
- *Root description.*—Fibrous, fleshy, white.

Leaves:
- *Immature leaf.*—Color: Upper surface: RHS 137A. Lower surface: RHS 137C. Length: 3.0–3.5 cm. Width: 1.7–2.0 cm.
- *Mature leaf.*—Color: Upper surface: Closest to RHS 137A. Lower surface: Closest to RHS 137C. Length: 4.0–4.3 cm. Width: 2.3–2.6 cm. Shape: Ovate. Margin: Pinnatisect; incised. Apex: Acute. Base: Attenuate. Texture: Hirsute. Venation: Palmate. Venation color: RHS 144A.
- *Petioles.*—Length: 1.3–1.5 cm. Diameter: 0.2 cm. Color: RHS 144A. Texture: Hirsute.

Stems:
- *Color.*—RHS 143A.
- *Length.*—15.0–25.0 cm.
- *Diameter.*—0.2–0.3 cm.

*Internode length.*—1.0–2.0 cm.
*Texture.*—Hirsute.
*Stem anthocyanin.*—None.

Flower buds:
*Color when bud first showing color.*—RHS 71A.
*Shape.*—Linear.
*Diameter.*—0.2–0.25 cm.
*Length.*—1.0–1.2 cm.

Inflorescence:
*Blooming habit.*—Flowers continuously throughout the growing season.
*Lastingness of individual blooms.*—Moderate.
*Fragrance.*—None.
*Inflorescence type.*—Terminal raceme.
*Racemes.*—Number per plant: 15–30. Diameter: 5.0–6.0 cm. Depth: 3.0–4.0 cm.
*Peduncle.*—Color: RHS 143A. Diameter: 0.2 cm. Length: 3.0–3.5 cm. Texture: Hirsute; glandular hairs with a dark purple hue.

Flowers:
*Floret form.*—Salverform; sessile on raceme.
*Number of florets per raceme.*—30–40.
*Number of petals.*—Gamopetalous, five lobed.
*Immature flower.*—Color: Upper side: RHS 60A, but with more blue-red hues. Underside: RHS N57C. Diameter: 1.3–1.5 cm.
*Mature flower.*—Color: Upper side: Closest to RHS N57B, but deeper with more blue hue. Underside: RHS N57C. Diameter: 1.8–2.0 cm. Corolla: Color of throat hairs: RHS 51C. Tube length: 2.0–2.4 cm.
*Petals.*—Size: Length of one lobe: 0.8–0.9 cm. Width of one lobe: 0.6–0.7 cm. Lobe shape: Obcordate. Apex: Retuse. Base: Fused. Margin: Entire. Texture: Papillose.
*Sepals.*—5 sepals, margins are fused to each other along their length, with a transparent membrane of less than 0.1 cm in width, with one smaller sepal (0.8 cm) attached to the base of the calyx.
*Calyx.*—Color: RHS 144A but a little darker. Length: 2.0–2.1 cm. Width: 0.1–0.2 cm. Shape: Linear. Apex: Acute. Texture: Hirsute; glandular hairs with a purple hue.

Reproductive organs:
*Stamens.*—Anthers and filaments fused to upper half of corolla tube; four anthers with two pollen sacs per anther.
*Pollen.*—Amount: Moderate. Color: RHS 11D.
*Pistil.*—1.
*Pistil length.*—0.15 cm.
*Fruit/seed set.*—Does not freely set seed, but can produce 4 narrow nutlets, approximately 0.4 cm long and enclosed in the dried calyx.

Disease and insect resistance: Mildew tolerance.

COMPARISON WITH KNOWN CULTIVARS

'Rap Horose' differs from the female parent 'Babylon Red' (U.S. Plant Pat. No. 13,126) by having smaller flowers and a more upright, less spreading habit than 'Babylon Red'. 'Rap Horose' differs from the male parent '1352-1' (unpatented) by having a rose-colored flower rather than a purple-colored flower. In addition, 'Rap Horose' has a more upright, vigorous habit than '1352-1'.

'Rap Horose' differs from the commercial variety 'Bodcompin' (U.S. Plant Pat. No. 15,242) by having a rose-colored flower rather than a pink-colored flower. In addition 'Rap Horose' has a flatter, fuller habit, shorter internodes and a less incised leaf than 'Bodcompin'.

I claim:

1. A new and distinct cultivar of *verbena* plant as shown and described herein.

* * * * *